(12) United States Patent
Scheuermann et al.

(10) Patent No.: US 7,582,112 B2
(45) Date of Patent: *Sep. 1, 2009

(54) METAL STENT WITH SURFACE LAYER OF NOBLE METAL OXIDE AND METHOD OF FABRICATION

(75) Inventors: Torsten Scheuermann, Munich (DE); Lutz Stehling, Aachen (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/952,624

(22) Filed: Dec. 7, 2007

(65) Prior Publication Data
US 2008/0147167 A1    Jun. 19, 2008

Related U.S. Application Data

(62) Division of application No. 10/364,112, filed on Feb. 10, 2003, now Pat. No. 7,402,173.

(51) Int. Cl.
A61F 2/06 (2006.01)
A61F 2/24 (2006.01)

(52) U.S. Cl. .................................. 623/1.46
(58) Field of Classification Search ............... 623/1.46, 623/1.42, 1.44; 606/108, 194
See application file for complete search history.

(56) References Cited

U.S. PATENT DOCUMENTS 3,282,690 A    11/1966  Delgrosso et al.

(Continued)

FOREIGN PATENT DOCUMENTS

DE    298 10 483    11/1999

(Continued)

OTHER PUBLICATIONS

PCT International Search Report in PCT/US04/03645 mailed Aug. 4, 2004.

(Continued)

*Primary Examiner*—Vy Q Bui
(74) *Attorney, Agent, or Firm*—Fish & Richardson P.C.

(57) ABSTRACT

In a process for producing a biocompatible stent, a tubular substrate of the stent adapted for diametric expansion has a layer of a noble metal oxide formed over at least the outer surface of greater diameter of the substrate, the substrate being composed of a metal or an alloy thereof that is non-noble or less-noble than the layer's noble metal. An interface region adapted to prevent corrosion and to provide a firm bond between the surface of the substrate and the noble metal oxide layer is established, at least in part, by forming the noble metal oxide layer with a progressively varying concentration of noble metal-to-oxide with depth of the layer such that a surface of pure noble metal and negligible oxide of the layer is in closest proximity to the surface of the substrate. In one embodiment of the process, the interface region is established by forming the surface of pure noble metal and negligible oxide thereof in direct contact with the metal or alloy of the substrate surface. In another, the interface region is established by first creating an oxide of the substrate metal or alloy thereof at the substrate surface, and then forming the noble metal oxide layer as above, but in contact with the substrate metal or alloy oxide. Alternatively, the noble metal oxide layer has no progressively varying concentration but simply overlies an oxide of the substrate metal or alloy.

4 Claims, 2 Drawing Sheets

U.S. PATENT DOCUMENTS

| | | |
|---|---|---|
| 3,296,038 A | 1/1967 | Bradley et al. |
| 3,346,379 A | 10/1967 | Rhodin |
| 3,969,186 A | 7/1976 | Thompson et al. |
| 4,487,637 A | 12/1984 | Padamsee |
| 4,778,461 A | 10/1988 | Pietsch et al. |
| 5,496,359 A | 3/1996 | Davidson |
| 5,588,443 A | 12/1996 | Davidson |
| 5,607,463 A | 3/1997 | Schwartz et al. |
| 5,628,787 A | 5/1997 | Mayer |
| 5,630,840 A | 5/1997 | Mayer |
| 5,643,794 A | 7/1997 | Liu et al. |
| 5,647,858 A | 7/1997 | Davidson |
| 5,653,691 A | 8/1997 | Rupp et al. |
| 5,679,470 A | 10/1997 | Mayer |
| 5,693,066 A | 12/1997 | Rupp et al. |
| 5,716,981 A | 2/1998 | Hunter et al. |
| 5,749,919 A | 5/1998 | Blanc |
| 5,758,562 A | 6/1998 | Thompson |
| 5,759,474 A | 6/1998 | Rupp et al. |
| 5,772,864 A | 6/1998 | Moller et al. |
| 5,800,511 A | 9/1998 | Mayer |
| 5,810,871 A | 9/1998 | Tuckey et al. |
| 5,824,077 A | 10/1998 | Mayer |
| 5,843,168 A | 12/1998 | Dang |
| 5,851,222 A | 12/1998 | Taylor et al. |
| 5,886,026 A | 3/1999 | Hunter et al. |
| 5,888,201 A | 3/1999 | Stinson et al. |
| 5,899,934 A | 5/1999 | Amundson et al. |
| 5,913,871 A | 6/1999 | Werneth et al. |
| 5,913,896 A | 6/1999 | Boyle et al. |
| 5,931,867 A | 8/1999 | Hanindl |
| 5,957,974 A | 9/1999 | Thompson et al. |
| 5,994,341 A | 11/1999 | Hunter et al. |
| 6,013,854 A | 1/2000 | Moriuchi |
| 6,019,786 A | 2/2000 | Thompson |
| 6,056,906 A | 5/2000 | Werneth et al. |
| 6,068,623 A | 5/2000 | Zadno-Azizi et al. |
| 6,099,561 A | 8/2000 | Alt |
| 6,106,530 A | 8/2000 | Harada |
| 6,110,204 A | 8/2000 | Lazarov et al. |
| 6,124,779 A | 9/2000 | Yamamoto |
| 6,136,023 A | 10/2000 | Boyle |
| 6,156,064 A | 12/2000 | Chouinard |
| 6,174,316 B1 | 1/2001 | Tuckey et al. |
| 6,183,508 B1 | 2/2001 | Stinson et al. |
| 6,187,037 B1 | 2/2001 | Satz |
| 6,200,256 B1 | 3/2001 | Weinberger |
| 6,200,685 B1 | 3/2001 | Davidson |
| 6,203,732 B1 | 3/2001 | Clubb et al. |
| 6,210,312 B1 | 4/2001 | Nagy |
| 6,210,437 B1 | 4/2001 | Frautschi |
| 6,217,503 B1 | 4/2001 | Weinberger et al. |
| 6,238,491 B1 | 5/2001 | Davidson et al. |
| 6,251,135 B1 | 6/2001 | Stinson et al. |
| 6,264,688 B1 | 7/2001 | Herklotz et al. |
| 6,287,332 B1 | 9/2001 | Bolz et al. |
| 6,340,367 B1 | 1/2002 | Stinson et al. |
| 6,340,368 B1 | 1/2002 | Verbeck |
| 6,342,068 B1 | 1/2002 | Thompson |
| 6,375,628 B1 | 4/2002 | Zadno-Azizi et al. |
| 6,379,380 B1 | 4/2002 | Satz |
| 6,383,217 B1 | 5/2002 | Satz |
| 6,387,121 B1 | 5/2002 | Alt |
| 6,394,945 B1 | 5/2002 | Chan et al. |
| 6,402,859 B1 | 6/2002 | Ishii et al. |
| 6,447,550 B1 | 9/2002 | Hunter et al. |
| 6,451,052 B1 | 9/2002 | Burmeister et al. |
| 6,468,219 B1 | 10/2002 | Njemanze |
| 6,478,815 B1 | 11/2002 | Alt |
| 6,485,507 B1 | 11/2002 | Walak et al. |
| 6,500,203 B1 | 12/2002 | Thompson et al. |
| 6,503,272 B2 | 1/2003 | Duerig et al. |
| 6,506,411 B2 | 1/2003 | Hunter et al. |
| 6,509,094 B1 | 1/2003 | Shah et al. |
| 6,527,802 B1 | 3/2003 | Mayer |
| 6,527,938 B2 | 3/2003 | Bales et al. |
| 6,530,947 B1 | 3/2003 | Euteneuer et al. |
| 6,537,310 B1 | 3/2003 | Palmaz et al. |
| 6,549,951 B1 | 4/2003 | Hui et al. |
| 2001/0001317 A1 | 5/2001 | Duerig et al. |
| 2001/0032013 A1 | 10/2001 | Marton |
| 2002/0042645 A1 | 4/2002 | Shannon |
| 2002/0138133 A1 | 9/2002 | Lenz et al. |
| 2002/0165600 A1 | 11/2002 | Banas et al. |

FOREIGN PATENT DOCUMENTS

| | | |
|---|---|---|
| EP | 0 601 804 | 6/1994 |
| EP | 0 688 545 | 12/1995 |
| EP | 0 810 889 | 2/1996 |
| EP | 0 788 802 | 8/1997 |
| EP | 0 799 607 | 10/1997 |
| EP | 0 803 233 | 10/1997 |
| EP | 0 804 909 | 11/1997 |
| EP | 0 855 171 | 7/1998 |
| EP | 0 873 734 A | 10/1998 |
| EP | 0 884 029 | 12/1998 |
| EP | 0 890 346 | 1/1999 |
| EP | 0 966 979 | 12/1999 |
| EP | 1 046 722 | 10/2000 |
| EP | 1 087 034 | 3/2001 |
| EP | 1 254 673 | 6/2002 |
| EP | 1 222 901 | 7/2002 |
| EP | 1 247 537 | 10/2002 |
| EP | 0 854 693 | 11/2002 |
| EP | 1 281 374 | 2/2003 |
| EP | 1 293 219 | 3/2003 |
| EP | 1 304 092 | 4/2003 |
| EP | 1 281 374 | 7/2003 |
| JP | 2000-14794 A | 1/2000 |
| WO | WO 94/16646 | 8/1994 |
| WO | WO 95/11055 | 4/1995 |
| WO | WO 95/18585 | 7/1995 |
| WO | WO 95/27092 | 10/1995 |
| WO | WO 95/30384 | 11/1995 |
| WO | WO 95/31945 | 11/1995 |
| WO | WO 96/24860 | 8/1996 |
| WO | WO 96/25960 | 8/1996 |
| WO | WO 96/38594 | 12/1996 |
| WO | WO 97/07740 | 3/1997 |
| WO | WO 97/13475 | 4/1997 |
| WO | WO 97/19723 | 6/1997 |
| WO | WO 97/45105 | 12/1997 |
| WO | WO 98/42390 | 10/1998 |
| WO | WO 98/43550 | 10/1998 |
| WO | WO 98/48732 | 11/1998 |
| WO | WO 99/47076 | 9/1999 |
| WO | WO 99/45161 | 10/1999 |
| WO | WO 99/51299 | 10/1999 |
| WO | WO 99/58184 | 11/1999 |
| WO | WO 99/62624 | 12/1999 |
| WO | WO 00/54836 | 9/2000 |
| WO | WO 00/61203 | 10/2000 |
| WO | WO 00/64506 | 11/2000 |
| WO | WO 00/68448 | 11/2000 |
| WO | WO 00/69359 | 11/2000 |
| WO | WO 00/72893 | 12/2000 |
| WO | WO 00/78394 | 12/2000 |
| WO | WO 00/78395 | 12/2000 |
| WO | WO 01/08600 | 2/2001 |
| WO | WO 01/21229 | 3/2001 |
| WO | WO 01/35865 | 5/2001 |
| WO | WO 01/41826 | 6/2001 |
| WO | WO 01/55473 | 8/2001 |

| | | |
|---|---|---|
| WO | WO 01/72349 | 10/2001 |
| WO | WO 02/05863 | 1/2002 |
| WO | WO 02/26271 | 4/2002 |
| WO | WO 02/26281 | 4/2002 |
| WO | WO 02/28458 | 4/2002 |
| WO | WO 02/30271 | 4/2002 |
| WO | WO 02/38080 | 5/2002 |
| WO | WO 02/43787 | 6/2002 |
| WO | WO 02/060506 | 8/2002 |
| WO | WO 02/076349 | 10/2002 |
| WO | WO 02/078762 | 10/2002 |
| WO | WO 02/080815 | 10/2002 |
| WO | WO 02/087473 | 11/2002 |
| WO | WO 03/003943 | 1/2003 |
| WO | WO 03/008657 | 1/2003 |
| WO | WO 03/001337 | 2/2003 |
| WO | WO 03/015662 | 2/2003 |
| WO | WO 03/018969 | 3/2003 |
| WO | WO 03/023401 | 3/2003 |

OTHER PUBLICATIONS

PCT International Search Report in PCT/US03/26008 mailed Feb. 5, 2004.

ASM International, Materials Park, Ohio, Properties and Selection: Nonferrous Alloys and Special Purpose Materials: "Preparation and Characterization of Pure Metals," 1990, 2:1093-1097.

Vrolix et al., "Heparin-coated Wiktor stents in human coronary arteries (MENTOR trial). MENTOR Trial Investigators," *Am. J. Cardiol.*, 2000, 86:385-389.

METAL STENT WITH SURFACE LAYER OF NOBLE METAL OXIDE AND METHOD OF FABRICATION

CROSS REFERENCE TO RELATED APPLICATIONS

This application is a divisional of application Ser. No. 10/364,112, filed Feb. 10, 2003.

BACKGROUND OF THE INVENTION

The present invention relates generally to body implantable stents, deployed in a vessel, tract, channel or duct, such as a coronary artery or femoral artery of a patient to maintain its lumen open for satisfactory blood flow therethrough, and more particularly to methods of producing multi-layer stent structures in which an oxide of a noble metal or alloy is bonded in a firm and stable relationship to an underlying non-noble or less-noble metal, and to such stent structures themselves.

When inserted and deployed in a vessel, duct, channel or tract (referred to generally herein, for convenience, as a vessel) of the body—for example, a coronary artery after dilatation of the artery by balloon angioplasty—a stent acts as a scaffold to maintain the vessel's lumen open. The stent prosthesis is structured as an open-ended tubular element with through-holes in its sidewall to allow expansion of its diameter from a first sufficiently small size to permit navigation of the stent, mounted on a balloon catheter, through the vessel to the target site where it is to be deployed, to a second fully deployed sufficiently large size to engage the inner lining of the vessel's wall for retention at the target site.

A coronary artery, for example, may become occluded from a buildup of fatty deposits or plaque on the inner lining of the vessel's wall. The artery blockage may be detected through an electrocardiogram performed during the individual's visit to a doctor, or be so extreme as to result in angina or even myocardial infarction. Typically, the procedure performed to relieve the blockage is balloon angioplasty, in which a balloon catheter is inserted into the vessel until the balloon is at the target site as monitored under fluoroscopy, the balloon is inflated to compress the fatty deposits against the inner lining of the vessel wall to open the lumen, and the catheter is then withdrawn from the patient. Other procedures may alternatively be performed for relieving the blockage, but for a relatively large percentage of angioplasty patients a new blockage of the treated vessel typically occurs only a few months later. The new blockage is usually attributable to trauma to the vessel wall that arises from the original angioplasty procedure, but the mechanism responsible for this restenosis or re-occlusion of the vessel lumen is intimal hyperplasia, a rapid proliferation of smooth muscle cells along the treated region of the vessel wall, quite different from the causation of the original blockage.

As noted above, it is customary to install a stent at the trauma site to maintain the vessel lumen open, often in a procedure accompanying or shortly after the angioplasty procedure. The stent is mounted in a crimped state on the balloon of a balloon catheter for advancement through the appropriate portion of the patient's cardiovascular system to the target site, also under x-ray fluoroscopy, where the balloon is inflated to deploy the stent by expansion of the stent diameter under the outwardly directed radial pressure exerted by the balloon. The outer surface of the stent is thereby forced into engagement with and exerts pressure on the inner lining of the vessel wall. The stent structure has sufficient resilience to allow some contraction of the diameter of the stent under the force exerted on it by the natural recoil of the vessel wall, but has sufficient stiffness to largely withstand the recoil and hold open the lumen of the vessel at the implant site.

The presence of the stent in contact with the vessel wall, however, can promote hyperplasia and resulting restenosis, and, along the stent's inner surface, may promote thrombus formation with the perfusion of blood through the stent's lumen. To avoid acute blockage of the vessel lumen owing to these reactions in some patients, drug coated stents are being prescribed on an almost regular basis. The outer surface of the stent to be implanted may be coated with an antiproliferative or immunosuppressive agent, while the inner surface may be coated with an antithrombotic agent. Drug coated stents are considerably more expensive than uncoated stents, and may be unnecessary for a relatively large percentage of angioplasty patients in which they are implanted, being prescribed solely to avoid the possibility of an undesirable reaction soon thereafter.

On the other hand, the use of uncoated stents has its own set of problems even beyond possibly inducing a traumatic response along the vessel wall or promoting thrombosis along the stent's lumen. The material of which the stent is composed can induce an allergic reaction in a statistically significant percentage of the patient population. These include commonly used stent materials such as chrome, nickel, and even medical grade 316L stainless steel—which contains about 16% nickel. Stent implants are contraindicated in many such allergic patients. Wholly biodegradable stents of possibly sufficient radial strength are undergoing testing but appear unlikely to constitute a breakthrough or a satisfactory solution in these cases.

Another consideration in material selection is the need for the implanting physician to be able to see the advancement and positioning of the stent as it is being implanted at the specified target site in the body, typically by x-ray fluoroscopy. The thickness of a metallic stent wall is made sufficient to withstand the aforementioned vessel wall recoil that invariably follows stent deployment and to hold the vessel lumen open. But it is also necessary that the calculation of stent wall thickness take into account the dimension necessary to render the stent visible with fluoroscopy, given the type of material of which the stent is composed. Various materials, such as 316L stainless steel, possess suitable mechanical strength to maintain an open vessel lumen, with smaller wall thickness than is required to provide fluoroscopic visibility. Typical conventional stent wall or wire thicknesses have ranged up to about 200 microns (or micrometers, $\mu m$). A 70 to 80 $\mu m$ thick 316L steel stent, for example, offers sufficient mechanical strength for the aforementioned purposes, but is too thin to create the shadow needed for fluoroscopic viewing because the x-ray absorption of this metal is so low. Increasing the wall thickness of the stent to enhance its radiopacity makes the stent less flexible, which adversely affects its maneuverability through narrow vessels during implantation, and its ease of expansion during deployment, with concomitant increased risk of balloon rupture.

It follows that for successful interventional use, the stent should possess characteristics of relatively non-allergenic reaction, good radiopacity, freedom from distortion on magnetic resonance imaging (MRI), flexibility with suitable elasticity to be plastically deformable, resistance to vessel recoil, sufficient thinness to minimize obstruction to flow of blood (or other fluid or material in vessels that require stenting other than the cardiovascular system), and biocompatibility to avoid vessel re-occlusion. Stent material, as well as stent design, plays a role in achieving these characteristics.

Aside from vascular usage, other vessels of the human body in which a stent might be installed to maintain an open lumen include the tracheo-bronchial system, the biliary hepatic system, the esophageal bowel system, and the urinary tract, to name a few. Many of the same requirements are found in these other endoluminal usages of stents.

Despite improvements in the design, construction and coating of coronary stents, restenosis remains a problem. A major contributing factor is the inability of the body to quickly incorporate the implanted foreign material of the stent. Basic research with cell cultures, as well as animal experiments, demonstrate that the degree of endothelialization of the foreign body is a determinant of the amount of the restenosis caused by the presence of that body. It had been assumed by industry practitioners and researchers that a highly polished and smooth surface is beneficial to prevent stent thrombosis and to facilitate endothelialization, but more recent experiments indicate this may not be entirely true.

A main reason for the lack of sufficient clinical success rate with electropolished stents is that the smooth muscle cells that seek to envelop a foreign body must undergo greater proliferation to cover the polished stent. The continuing flow of blood with high pressure and high shearing stress prevents the migration of smooth muscle cells that proliferate from the media and adventitial cells of a stented vessel such as a coronary artery. Indeed, a slightly rough surface appears to facilitate considerably more coverage by smooth muscle cells, which leads to a functional endothelial layer some 10 to 14 days after stent implantation. A single layer of endothelial cells has been found to seal the neointima, and thereby to prevent the stimulus that facilitates proliferation of cells beyond mere coverage of the foreign body.

As is intuitively obvious, the thinner the stent strut, the less wall thickness of the stent invades the lumen of the stented vessel. And a thin stent is more easily covered by a neoendothelial build-up. Accordingly, it is desirable to make the stent wall as thin as possible. But, again, fluoroscopic visibility of the structure has a role in determining its thickness for a given material.

Some improvement in visibility is achieved by application of an adherent, more radiopaque layer to the surface of a stent core material of medical grade implantable 316L stainless steel. These radiopaque layer materials include gold and certain other noble metals, such as platinum. Their considerably greater radiopacity relative to stainless steel renders the stent highly visible under fluoroscopy. The materials are also substantially non-allergenic and non-thrombogenic. The coating may be applied in a very thin layer, leaving the determinant of stent wall thickness almost solely the requirement of mechanical strength. The coating must be capable of absolute adherence to the underlying metal of the stent to avoid cracking or defects in the homogeneous overlying layer, and sufficient resistance to peeling or flaking of the coating material both during insertion of the stent, expansion of the diameter of the stent as it is being deployed in final position, and throughout the entire time the stent remains in that position—objectives which are not easily achievable. The presence of cracks or related defects in the surface coating can produce a galvanic potential that could ultimately lead to corrosion of the underlying steel or lesser metal, an unacceptable situation for a device intended to be permanently implanted in the body. Therefore, manufacturing requires a high degree of quality control and concomitant high cost.

U.S. Pat. No. 6,099,561, of the same assignee, discloses a stent structure with three fundamental layers, a first underlying substrate of a stent metal that functions to provide high mechanical strength, a second intermediate layer that functions to provide high fluoroscopic visibility—such as a noble metal layer or alloy thereof—, and a top layer of a particularly beneficial biocompatible material—designated to be a ceramic-like material such as iridium oxide or titanium nitride. The intermediate layer of elemental noble metal or an alloy thereof is uninterrupted by gaps or pockets along its length, and is highly adherent for tight coverage and substantially uniform thickness. This intermediate layer tends to avoid the creation of a galvanic potential that would lead to corrosion of the lesser, underlying metal. Such a condition might otherwise exist if, without the presence of an intermediate uninterrupted noble metal layer, a layer of ceramic-like metal were to overlie and adhere to the base metal at points where fissures could exist. The multi-layer stent of the '561 patent exhibits mechanical strength, small physical dimensions, increased visibility, long-term stability, and a highly biocompatible surface that enables rapid endothelialization with low occurrence of restenosis. But it is expensive to produce.

U.S. Pat. No. 6,387,121, of the same assignee as the present application, discloses a multi-layer stent with a thin, continuous intermediate layer of metal or alloy of niobium, zirconium, titanium or tantalum overlying the surface of the stent's tubular metal base, and an outer layer of iridium oxide overlying the intermediate layer with interstices for storing and dispensing (eluting) drugs.

U.S. Pat. No. 6,478,815, also assigned to the same assignee as this application, discloses a stent composed of niobium with a trace of another metal, such as zirconium, titanium or tantalum for alloy formation and reinforcement. Also, a surface coating of iridium oxide or titanium nitrate may be applied to the niobium structure to aid in inhibiting vessel closure, as with the previous patent disclosures mentioned herein. This stent is beneficial, enjoying many of the advantages that have been sought as discussed above, with only two layers in the stent structure.

A stability problem may be encountered in the bond between the noble metal oxide layer, such as iridium oxide, and a non-noble or less-noble metal, alloy or compound, such as niobium or platinum enriched medical grade stainless steel. During the bonding process the less noble metal tends to draw or leach oxygen atoms from the noble metal, which causes depletion of oxygen from the latter metal. The result can be a less stable, less satisfactory bond or adhesion between the two layers. In addition, in the case of an iridium oxide layer as the noble metal oxide, the oxygen depletion leaves that layer less effective as a stenosis or restenosis inhibitor.

SUMMARY OF THE INVENTION

Therefore, it is a principal goal of the present invention to provide a body-implantable stent, and method of production thereof, in which a noble metal oxide surface coating on a stent having either a non-noble or a less-noble (than the surface coating) metal or alloy substrate or core maintains desired characteristics and has an improved bond to the underlying substrate.

According to the invention, in a process for producing a stent having multiple layers, a tubular substrate or core of the stent is composed of a less-noble or non-noble metal or alloy, such as niobium or platinum-enriched medical grade stainless steel; an interface region is formed at a surface of the substrate or the confronting surface of the layer of iridium oxide to be deposited thereon, the interface region having characteristics preselected to prevent corrosion and to provide a firm bond between the surface of the substrate and the noble metal oxide layer when deposited thereon, and the noble metal oxide layer is then deposited on the surface of the substrate at the location where the interface region is formed.

In an exemplary process for producing a biocompatible stent based on that concept, a tubular substrate adapted for diametric expansion, a layer of a noble metal oxide is formed over at least the outer surface of greater diameter of the substrate, the substrate being composed of a metal or an alloy thereof that is non-noble or less-noble than the noble metal, and at least partly establishing an interface region adapted to prevent corrosion and to provide a firm bond between the surface of the substrate and the noble metal oxide layer by forming the noble metal oxide layer with a progressively varying concentration of noble metal-to-oxide with depth of said layer such that a surface of pure noble metal and negligible oxide of said layer is in closest proximity to the surface of the substrate.

In one embodiment or technique, the process may include establishing the interface region solely by forming the noble metal oxide layer with the surface of pure noble metal and negligible oxide thereof in direct contact with the metal or alloy of the surface of the substrate. In another, the process may include establishing the interface region by first creating an oxide of the metal or alloy thereof at the surface of the substrate to a thickness in a range from approximately 1 nm to approximately 500 nm, and then forming the noble metal oxide layer with the surface of pure noble metal and negligible oxide thereof overlying the oxide of the metal or alloy thereof at the surface of the substrate. In still another, the process may include establishing the interface region by first creating either a nitric oxide or nitride of the metal or alloy thereof at the surface of the substrate to a thickness in a range from approximately 1 nm to approximately 500 nm, and then forming the noble metal oxide layer with the surface of pure noble metal and negligible oxide thereof overlying the nitric oxide or nitride of the metal or alloy thereof at the surface of the substrate. And in yet another embodiment or technique, the process may include establishing the interface region by first creating an intermediate layer of either a nitric oxide or nitride of the noble metal to a thickness in a range from approximately 1 nm to approximately 500 nm overlying the surface of the substrate, and then forming the noble metal oxide layer with the surface of pure noble metal and negligible oxide thereof atop the intermediate layer.

Alternatively, the process may simply involve forming a noble metal oxide layer overlying and in direct contact with an oxide of the substrate metal or alloy thereof, without any progressively varying concentration of noble metal-to-oxide in the noble metal oxide layer. For example, an iridium oxide layer is applied onto an underlying substrate metal of non- or less-noble characteristic (for example, the aforementioned niobium or alloy thereof such as with an added trace of zirconium, titanium or tantalum, or the aforementioned platinum-enriched medical grade stainless steel) that has been oxidized in at least a surface region intended to receive the iridium oxide layer, for stable, non-corrosive bonding of the two. The desired oxidation of the less noble metal (or alloy thereof) can be achieved by heating in an oxygen-rich environment, reverse electro-polishing, or any other conventional method. Forming the noble metal oxide layer in a desired thickness on the exposed surface(s) of the stent may then be accomplished by any conventional technique, such as by physical vapor deposition, or by chemical wet processing, so as to produce the desired firm bond between the oxide layer and the underlying less noble metal or alloy by virtue of the presence of the oxide region in the latter (e.g., niobium oxide).

Oxidation of the less noble metal should be at least along the exposed surface region of the non- or less-noble metal substrate of the stent, if not throughout the thickness of the substrate. The existence of niobium oxide in a primarily niobium substrate, for example, inhibits leaching of oxygen from the overlying iridium oxide, and hence, maintains the desired characteristics of the iridium oxide layer for its essential purpose of biocompatibility and avoidance of irritation and consequent stenotic reaction of body tissue (such as the inner lining of an artery wall) with which that layer is in contact when the stent is implanted.

A coated stent according to the invention comprises a metallic substrate; and a coating of an oxide of noble metal overlying a surface region of the substrate. The surface region is one of (i) a substantially pure metal of lesser standing in the periodic table of elements than the noble metal, (ii) an alloy, oxide, nitride, or nitric oxide of the lesser metal, and (iii) a nitride or nitric oxide of the noble metal. The noble metal oxide coating progressively varies with thickness commencing at the surface region of the substrate, from a concentration of the noble metal of substantially 100% purity with negligible amount of oxide and other constituents, and ending at an opposite surface of the coating with a concentration of the noble metal oxide of stoichiometric equilibrium.

Another embodiment a multi-layer stent of the invention includes a tubular substrate composed primarily of a metal or alloy having the properties discussed above; an interface region at a surface of the substrate having characteristics to inhibit corrosion and establish a firm bond between the surface of the substrate and a noble metal oxide layer to be formed thereon; and the noble metal oxide layer coated on the interface region of the surface of the substrate.

BRIEF DESCRIPTION OF THE DRAWING

The above and other aims, goals, objectives, features, aspects and attendant advantages of the present invention will become apparent to those skilled in the art from a consideration of the following detailed description of a best mode presently contemplated of practicing the invention by reference to certain preferred exemplary embodiments and methods of manufacture thereof, taken in conjunction with the accompanying drawing, in which.

DETAILED DESCRIPTION OF BEST MODE OF PRACTICING THE INVENTION

Figure 1:
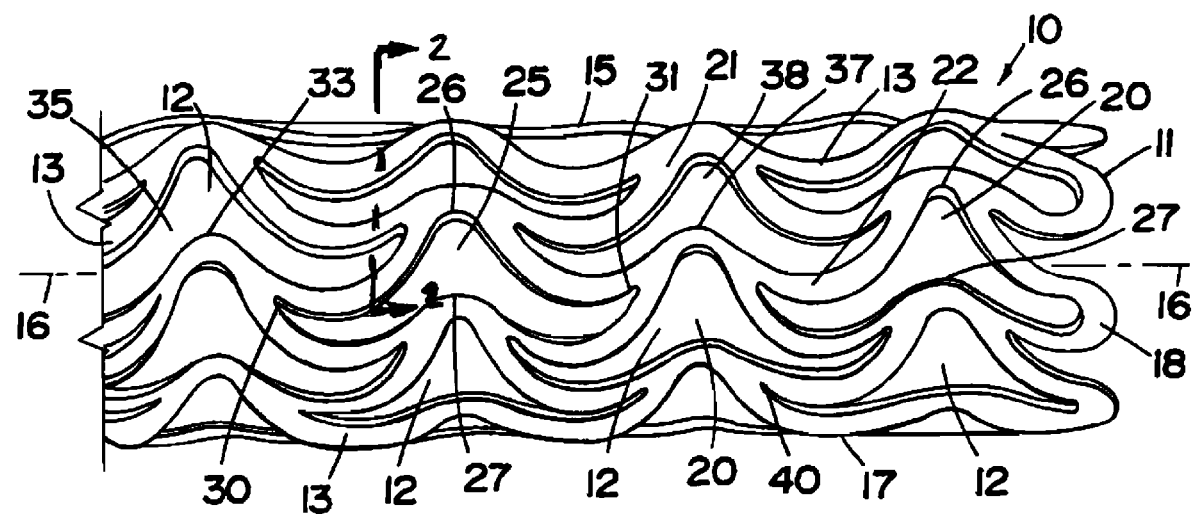
FIG. 1 is a side perspective view of an exemplary embodiment of a stent structure for use with the invention (in which the far side of the structure is not shown through openings on the near side, for the sake of simplicity and clarity)

It is to be understood that none of the drawing figures is intended to be a representation to scale of the respective depicted embodiment.

FIG. 1 is a perspective view of a stent 10 of hollow tubular self-supporting structure, with a substrate or core composed preferably of niobium (Nb) with a trace of zirconium (Zr), titanium (Ti) or tantalum (Ta), for example, preferably zirconium, the trace amount preferably being between approximately 1% and approximately 5%, and most preferably being about 2%, and remainder niobium. The added trace metal improves physical characteristics including strength of the stent for its intended function. Typically, the niobium stent material includes negligible amounts of tantalum (Ta, about 180 micrograms per gram (μg/g)), iron (Fe, <20 μg/g), silicon (Si, about <20 μg/g), tungsten (W, <20 μg/g), molybdenum (Mo, <20 μg/g), hafnium (Hf, <20 μg/g), carbon (C, about 7 μg/g), and nitrogen (N, about 53 μg/g), as well as amounts of hydrogen (H) and oxygen (O) primarily introduced during the processing. Alternatively, a stent substrate suitable for the present invention may be platinum-enriched (e.g., 20-30%) 316L medical grade stainless steel.

For a niobium stent substrate, the presently preferred process of fabricating the stent is performed in the following sequence of steps: (1)tube processing from Nb-1%Zr ingots; (2) laser cutting of tube; (3) mechanical and chemical finishing; (4) electropolishing; (5) vacuum annealing; and (6) anodizing or sputtering with a surface coating of iridium oxide.

In the laser cutting process, the tubular stent member is provided with a multiplicity of through-holes or openings 12 through sidewall 15, defined and bounded by a plurality of struts or links 13, which enables expansion of the stent diameter when the device is to be deployed at a target site in a vessel, channel, duct or tract (collectively, vessel) of the human body. Precise cutting of openings 12 to form a latticework sidewall is achieved using a conventional laser with narrow beam following a programmable pattern.

The exemplary type of structure shown in FIG. 1 is described in detail in patent U.S. Pat. No. 6,398,805 of the same assignee. This configuration provides a relatively very low coefficient of friction of the outer surface 17, for easier advancement of stent 10 in the vessel to a target site for deployment. The latticework sidewall 15 has a pattern of interconnected struts 13 optimized for orientation predominantly parallel to the longitudinal axis 16 of the tube 11. Substantially none of the struts are oriented perpendicular (i.e., transverse) to the axis 16. Thus, no strut interconnecting any other struts in the latticework is oriented to lie completely in a plane transverse to the longitudinal axis, without running from one end of the stent to the opposite end. The network or latticework of struts 13 defines a series of longitudinally repeating circumferential rows 20 of openings 12, with each opening bounded by alternating links in wavelets of higher and lower crests (or shallower and deeper troughs, if FIG. 1 is rotated 180°) in successive rows of each circumferential column displaced along the length of the cylindrical element.

Each pair of struts such as 21, 22 bounding an opening 12 in any given row 25 have the shape of circumferentially displaced wavelets with adjacent circumferentially aligned higher and lower crests 26, 27, respectively, in which the wavelets intersect (30) one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof.

When the stent 10 is crimped onto a small diameter (low profile) delivery balloon (not shown), the adjacent circumferentially aligned crests of each row move closer together, and these portions tend toward fitting into each other, as the pattern formed by the latticework of struts allows substantial nesting together of the crests and bows, which assures a relatively small circumference of the stent in the crimped condition. Such a stent is highly flexible, and is capable of undergoing bending to a small radius corresponding to radii of particularly tortuous coronary arteries encountered in some individuals, with circumferentially adjacent struts along the inner portion of the bend moving closer together while those along the outer portion of the bend spread further apart, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support of a scaffold provided by the stent when in its fully deployed condition. This assures a rigid structure which is highly resistant to recoil of the vessel wall following stent deployment. The particular configuration of the stent structure shown in FIG. 1, while highly desirable, is illustrative only.

The stent may be pre-opened after fabrication to relieve stresses. Pre-opening produces a stent inner diameter that allows the stent to slide comfortably over the uninflated mounting balloon, for ease of crimping the stent onto the balloon. Annealing may be performed after pre-opening by heating the stent structure to an appropriate temperature for a predetermined interval of time.

The presently preferred niobium/zirconium material of the stent is fabricated in any conventional manner for producing alloys, with the zirconium amounting from 1% to 5% by weight, preferably about 2%, and the remainder niobium. For example, the manufacturing process may be performed by sintering particles or microspheres of the constituent metals under heat and pressure. Rather than zirconium, a trace amount (e.g., one to three percent) of titanium or tantalum may be alloyed with niobium for added strength and other desirable physical characteristics. Other suitable alternative additive materials include those described in patents U.S. Pat. Nos. 5,472,794 and 5,679,815, for example. The alloy is then formed into tubing and the through holes are provided in its side wall as described above.

The stent structure can be produced with a wall thickness of about 85 μm, which offers sufficient mechanical strength to resist the natural recoil of the blood vessel wall following deployment of the stent, as well as excellent visibility under fluoroscopy, but which does not obstruct the vessel lumen to any significant extent. This stent has little or no distortion in a process of magnetic resonance imaging (MRI), and is highly beneficial for noninvasive monitoring of cerebral and peripheral vessels also.

To enhance the biocompatibility and antiproliferative characteristics of the stent after implantation the surfaces may be coated with a 10 to 1000 nanometers (nm) thick layer of iridium oxide (sometimes referred to herein as IROX). This may be accomplished by any conventional process, such as physical vapor deposition (PVD). PVD encompasses a broad class of vacuum coating processes in which material is physically removed from a source by evaporation or sputtering or laser-induced sputtering, transported through a vacuum or partial vacuum by the energy of the vapor particles themselves or enhanced in an electric field, and condensed as a film on the surfaces of appropriately placed parts or substrates. Chemical compounds are deposited by either using a similar source material, or by introducing a reactive gas (nitrogen, oxygen, or simple hydrocarbons) containing the desired reactants, which react with metal(s) from the PVD source. In general, all PVD processes can be separated into three distinct phases, namely, (a) emission from a vapor source (target); (b) vapor transport in vacuum; and (c) condensation on substrates to be coated.

The easiest substrates to coat are those that are electrically conductive and remain stable (minimum outgassing or decomposition of bulk material) at elevated temperatures. With metal substrates, certain materials, surface conditions, and assembling techniques must be avoided to achieve good adhesion and film properties. For example, certain metallic alloys create problems during coating if the temperature exceeds a predetermined temperature (e.g., 390° F., equivalent to 200° C.) because of their high vapor pressures. Porous metals are generally difficult to coat because oils and contaminants remain entrapped in the pores. Burrs must be removed from the substrate before coating to prevent exposure of uncoated metal when the burrs are later removed. Although some materials and assembly methods are undesirable for PVD coatings, many of the problems described above can be overcome by thorough cleaning and by appropriate adjustment of operating parameters. However, since stents are basically tubes with holes and slots, their configuration makes vapor deposition on the inner surfaces difficult.

Figure 2:
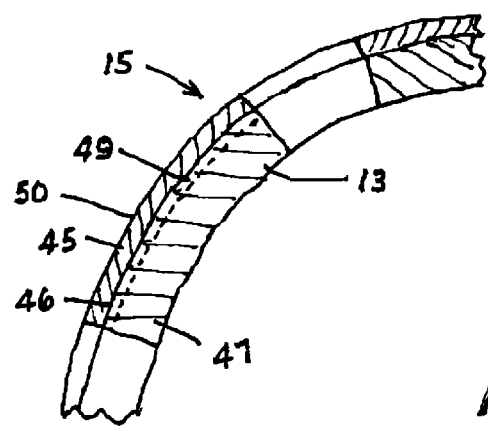
FIG. 2 is an enlarged partial cross-sectional view through the lines 2-2 of the exemplary embodiment of FIG. 1, with greatly exaggerated layer thicknesses.

Process conditions for an exemplary embodiment or technique to deposit IROX on stents composed of Nb metal or Nb-based alloys, shown in FIG. 2, are as follows:

a. The sputter target is iridium.
b. The stent substrates are affixed on small hooks, and undergo continuous movement similar to the satellite cog of an planetary gear. Because the iridium ion stream is one-dimensional, the planetary movement assures an IROX layer of homogeneous thickness and quality from the deposition process.
c. The recipient is evacuated.
d. The substrate is plasma etched, with preparation and minimal abrasion of the natural oxide layer on Nb alloys typically being a few nanometers thick.
e. $O_2$ is introduced as reactive gas by keeping the stoichiometric ratio of the resulting IROX coating.
f. Deposition is commenced by accelerating Ar ions onto the iridium target, and vaporization of Ir starts.
g. Ir vapor moves toward the plural stent substrates and becomes ionized.
h. Shortly before reaching the substrate surface Ir ions react with $O_2$ to form $IrO_2$ (hence, the name "reactive sputtering").
i. The kinetic energy of the ion stream makes the $IrO_2$ deposition dense and adhere sufficiently to the substrate surface.
j. The process is completed when an $IrO_2$ layer 45 of desired thickness in a range between about 10 to about 1000 nanometers is deposited on the surface 46 of substrate 47.

The relative thicknesses of the layers are greatly exaggerated in FIG. 2, and the surfaces, particularly the exposed surface of IROX layer 45, are shown as being smooth merely for the sake of simplicity.

Another process that may be used for forming an iridium oxide layer is conventional chemical deposition. Niobium and its alloys reduce $IrO_2$ to Ir+metal-oxide because of their high affinity to oxygen. This effect occurs even during the deposition of $IrO_2$ when the last coating step transforms the precipitation of $Ir_2O_3$ on the stent surface in Ir+$IrO_2$ after a last baking step. In the reaction, then, only Ir is deposited on the surface of the Nb substrate, rather than $IrO_2$, as the less-noble metal, Nb, becomes oxidized on its surface beneath the Ir coating.

To avoid reducing $Ir_2O_3$ to Ir+metal oxide, any of the following procedures may be employed: (1) the surface of the less-noble metal may be protected with a zone where the affinity to oxygen is low; or (2) an additional oxide layer may be produced by pre-anodizing or -passivating the Nb substrate; or (3) using organic iridium compounds instead of a sonolysis method as described in either of publications DE 19916315A1 (Germany) or WO99/52471 (WIPO); or (4) coating the non- or less-noble metal with a noble metal as described in either of the latter publications.

Galvanic corrosion may be encountered when the coating material differs from the substrate material, and especially when noble and non- or less-noble metals are electrically connected by the relationship of coating overlying the substrate, and then used in electrolytes such as blood or water. If the coating becomes cracked because of mechanical stress, the metallic ions can get in solution into the electrolyte and cause corrosion of the substrate with attendant weakening of the bond with the coating.

In the case of a substrate metal such as Nb or an alloy thereof and the deposited oxide of the noble element iridium, $IrO_2$, a similar process may occur. In brief, the high affinity of non-noble or less-noble metals to oxygen may reduce $IrO_2$ to Ir and oxygen in the interface area between the substrate and the coating thereon as the latter is deposited. This could possibly result in decreased adhesion over time, and lead to flaking of the deposited $IrO_2$ layer.

Figure 3:
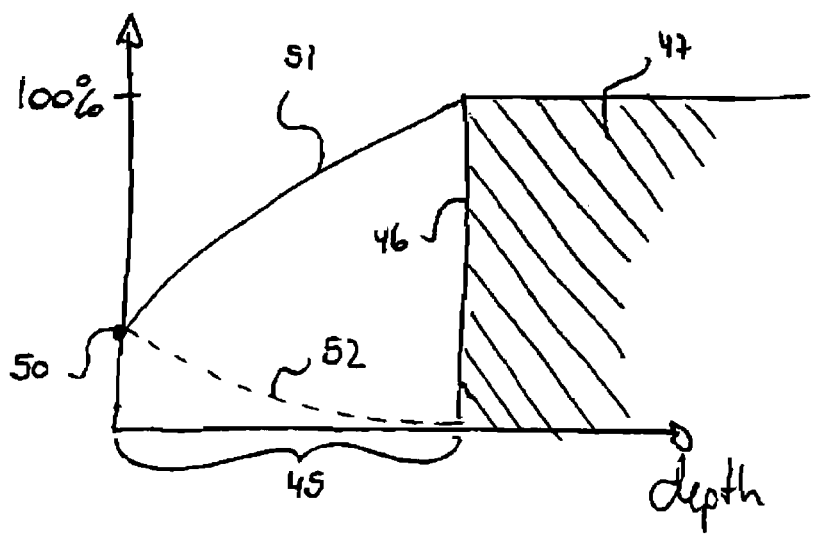
FIGS. 3, 4 and 5 are still further enlarged partial cross-sectional views through the stent's substrate surface region, interface region and overlying noble metal oxide layer of three exemplary embodiments, with greatly magnified layer thicknesses, and in which the noble metal oxide layer is depicted as a diagram of noble metal concentration versus depth (or thickness) of the layer.
Figure 4:
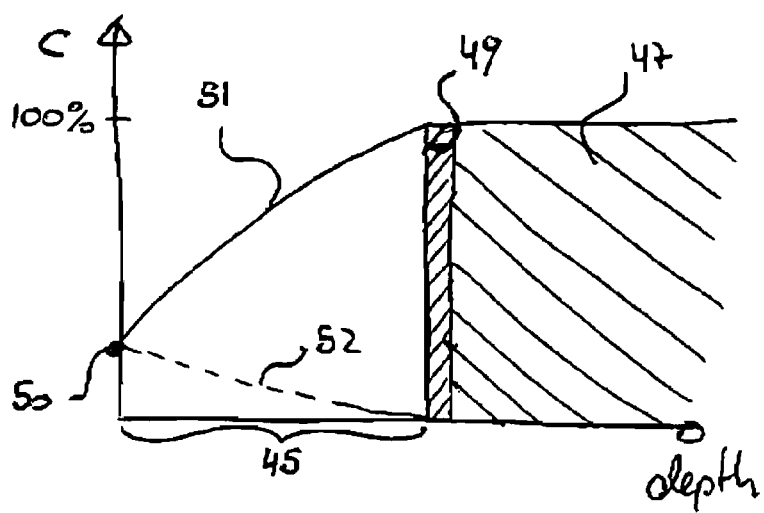
Figure 5:
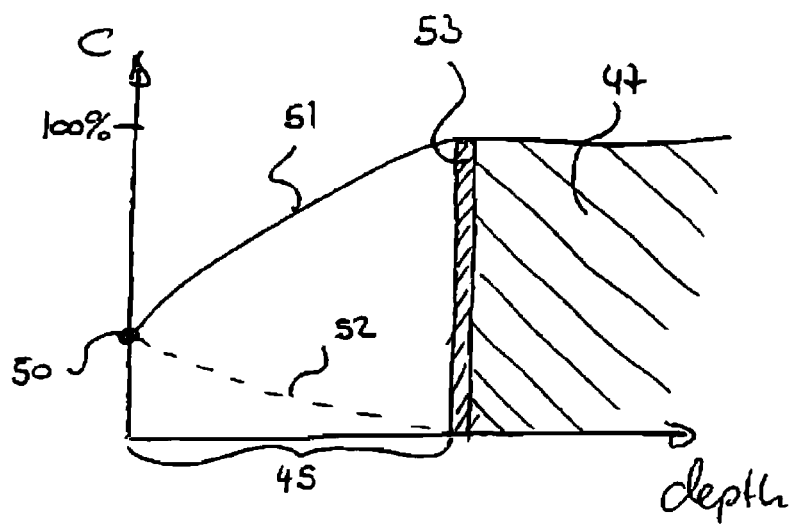

FIGS. 3, 4 and 5 are additional enlarged partial cross-sectional views through the stent's substrate surface region, interface region and overlying noble metal oxide layer of three exemplary embodiments, with greatly magnified layer thicknesses, and in which the noble metal oxide layer is depicted as a diagram of noble metal concentration versus depth (or thickness) of the layer. That is, the layer designated 45 is a graphical depiction of how the iridium (in this example) concentration in the IROX layer varies progressively with the depth of the layer. In the chart or graph, the vertical (y) axis represents percentage concentration of a constituent, and the horizontal (x) axis represents depth (or thickness) of the structural component (in this case, the IROX layer), i.e., reference number 51 indicates concentration of Ir along the coating or layer depth. It is not to be taken as indicating that the width of the IROX layer undergoes a change with depth or thickness; rather, the width remains constant.

In each of FIGS. 3, 4 and 5 (and FIG. 2 as well), the following reference number indications apply: 45: IROX coating; 46: Ir layer; 47: niobium (Nb) substrate (non-noble or less-noble metal or alloy); 49: oxide of substrate 47; 50: stoichiometric equilibrium of $IrO_2$; 51: concentration of Ir along coating depth; 52: concentration of O along coating depth; 53: layer of Nb nitric oxide or Ir nitric oxide or Nb nitride or Ir nitride. On the graphical portion of the chart shown in the Figures, 51 shows that the concentration of Ir diminishes progressively with distance from the surface of the non-noble or less-noble substrate 47, which is in closest proximity to the maximum concentration of the Ir. It should be emphasized that reference number 50 is as stated above; it is not associated with a percentage concentration of any constituent of the layer on the y-axis.

According to the invention, the problems resulting from an attempted adhesion or bonding of two metals of different nobleness can be avoided by special preparation of the substrate, by either of two distinct and different means or techniques, as follows:

1. The non- or less-noble substrate (niobium, alloyed with the trace of zirconium or other metal as described above) is anodized before the noble metal oxide (e.g., IrO$_2$) layer is deposited. This can be a galvanic process where the substrate surface becomes oxidized and passivated, or the passivation is achieved by other means such as sputtering. An oxide surface region 49 of selected thickness in a range from about 1 to about 500 nanometers (nm) is formed on the substrate 47 by the anodizing step, and this surface becomes the interface for the subsequently deposited IROX layer coating, to protect the substrate from direct contact with IrO$_2$ (FIG. 4).
2. Alternatively, during the PVD process, a second preparation step (after plasma etching) is introduced, comprising a selected one of the following three alternatives:
    a. The partial pressure of the reactive gas oxygen is continuously increased from zero to the pressure keeping the stoichiometric ratio of IrO$_2$. The resulting IROX layer 45 progressively varies from virtually pure (substantially 100%) Ir on the substrate surface 46 to a greatest concentration of iridium oxide at the outer surface 50 of the coating. An interfacial reaction between oxides of the non- or less-noble substrate metal (e.g., Nb$_2$O$_5$—niobium pentoxide) and of the noble iridium is not possible. This protects the interface area from corrosion as well (FIG. 3).
    b. An interlayer of the substrate oxide (e.g., Nb$_2$O$_5$) is produced by using a double-target equipped PVD apparatus. One target is composed of the substrate material, and the other is composed of Ir. For coating a substrate oxide the process is similar to that run for IROX deposition, but using the target of substrate material. After achieving an oxide of selected thickness in a range from about 1 to about 500 nanometers the targets are flipped, continuing with the IROX coating.
    c. Introducing nitrogen as a second reactive gas produces an interlayer of a very resistant composition of metal nitric oxides or an alloy of metal nitrite and metal oxide 53 (FIG. 5). This is possible as substrate metal nitric oxide or nitrite and oxide using double-target PVD (e.g., Nb nitric oxide) or as Ir nitric oxide or Ir nitrite and oxide which is converted to IrO$_2$ by following the procedure described in 2.a., immediately above The affinity of niobium or Nb-based alloys to nitrogen is low, resulting in a more stable coating stack.

Although a best mode of practicing the invention has been disclosed by reference to a preferred method and embodiment, it will be apparent to those skilled in the art from a consideration of the foregoing description that variations and modifications may be made without departing from the spirit and scope of the invention. Accordingly, it is intended that the invention be limited only by the appended claims and the rules and principles of applicable law.

What is claimed is:

1. A multi-layer stent, comprising,
    an open-ended tubular metallic sidewall adapted to be expanded from a relatively small diameter adapted for advancement of the stent through a patient's body vessel to a deployment target site, to a relatively larger diameter for engaging the wall of said vessel to maintain an open lumen at said site;
    an iridium oxide outer layer of said stent about the larger diameter surface of said sidewall; and
    an interface bonding region along said larger diameter surface of said sidewall and said surface of the iridium oxide layer closest thereto, consisting of one of (1) an alloy, oxide, nitride, or nitric oxide of metal of said sidewall, and (ii) a nitride or nitric oxide of iridium; said sidewall metal being either non-noble or less noble than iridium.

2. The multi-layer stent of claim 1, wherein said sidewall metal is one of (i) niobium, (ii) niobium alloyed with a trace of zirconium, titanium or tantalum, or (iii) a metal either non-noble or less-noble than niobium.

3. The multi-layer stent of claim 1, wherein said interface bonding region has a thickness in a range from approximately 1 nm to approximately 500 nm.

4. The multi-layer stent of claim 1, wherein said iridium oxide layer has a thickness in a range from approximately 10 nm to approximately 1000 nm.

* * * * *

UNITED STATES PATENT AND TRADEMARK OFFICE
CERTIFICATE OF CORRECTION

PATENT NO. : 7,582,112 B2
APPLICATION NO. : 11/952624
DATED : September 1, 2009
INVENTOR(S) : Torsten Scheuermann Page 1 of 1

It is certified that error appears in the above-identified patent and that said Letters Patent is hereby corrected as shown below:

Column 1, line 5, please delete "CROSS REFERENCE" and insert --CROSS-REFERENCE-- therefor;

Column 12, line 17 (Claim 1), please delete "comprising," and insert --comprising:-- therefor;

Column 12, line 28 (Claim 1), please delete "(1)" and insert --(i)-- therefor;

Column 12, line 36 (Claim 2), please delete "less-noble" and insert --less noble-- therefor.

Signed and Sealed this

Tenth Day of November, 2009

David J. Kappos
*Director of the United States Patent and Trademark Office*